(12) United States Patent
Feldchtein

(10) Patent No.: US 7,538,886 B2
(45) Date of Patent: May 26, 2009

(54) COMMON PATH TIME DOMAIN OPTICAL COHERENCE REFLECTOMETRY/TOMOGRAPHY DEVICE

(75) Inventor: Felix I. Feldchtein, Cleveland, OH (US)

(73) Assignee: Imalux Corporation, Cleveland, OH (US)

( * ) Notice: Subject to any disclaimer, the term of this patent is extended or adjusted under 35 U.S.C. 154(b) by 69 days.

(21) Appl. No.: 11/466,240

(22) Filed: Aug. 22, 2006

(65) Prior Publication Data

US 2008/0049229 A1   Feb. 28, 2008

(51) Int. Cl.
*G01B 9/02* (2006.01)
(52) U.S. Cl. .................................... 356/497
(58) Field of Classification Search .......... 356/479, 356/497
See application file for complete search history.

(56) References Cited

U.S. PATENT DOCUMENTS 4,533,247 A * 8/1985 Epworth ..................... 356/479
5,555,087 A * 9/1996 Miyagawa et al. ........... 356/485
7,126,693 B2 * 10/2006 Everett et al. ............... 356/479

OTHER PUBLICATIONS

International Search Report and Written Opinion for International Application No. PCT/US07/76369 dated Mar. 27, 2008.

* cited by examiner

*Primary Examiner*—Hwa S Lee (Andrew)
(74) *Attorney, Agent, or Firm*—Renner, Otto, Boisselle & Sklar, LLP

(57) ABSTRACT

In common path time domain OCT/OCR devices optical radiation from a source is first split into two replicas, which are then delivered to an associated sample by an optical fiber probe. The tip of the optical fiber probe serves as a reference reflector and also serves as a combining element that produces a combination optical radiation by combining an optical radiation returning from the associated sample with a reference optical radiation reflected from the reference reflector. The topology of the devices eliminates the necessity of using Faraday mirrors, and also allows for registering a cross-polarized component of the optical radiation reflected or backscattered from the associated sample, as well as a parallel-polarized component.

16 Claims, 3 Drawing Sheets

COMMON PATH TIME DOMAIN OPTICAL COHERENCE REFLECTOMETRY/TOMOGRAPHY DEVICE

BACKGROUND OF THE INVENTION

The present invention relates to systems and methods for visualizing subsurface regions of samples, and more specifically, to a time domain optical coherence reflectometer (OCR) and time domain optical coherence tomography (OCT) device that provide internal depth profiles and depth resolved images of samples.

Optical coherence reflectometry/tomography involves splitting an optical radiation to at least two portions, and directing one portion of the optical radiation toward a subject of investigation. The subject of investigation will be further referred to as a "sample", whereas the portion of optical radiation directed toward the sample will be further referred to as a "sample portion" of optical radiation. The sample portion of optical radiation is directed toward the sample by means of a delivering device, such as an optical probe. Another portion of the optical radiation, which will be further referred to as "reference portion", is used to provide heterodyne detection of the low intensity radiation, reflected or backscattered from the sample.

Typically, any optical coherence reflectometer or OCT device is specified by a longitudinal (in-depth) range of interest, whereas the longitudinal range of interest and the sample overlap, at least partially. The longitudinal range of interest includes a proximal boundary and a distal boundary, and in time domain systems is equivalent to the longitudinal scanning range. In time domain optical coherence reflectometry, at every moment only a small part of the sample portion of the optical radiation, reflected or backscattered from some point located inside the boundaries of the longitudinal range of interest is utilized. In-depth profiling of the sample is provided by introducing a variable optical path length difference for the sample and reference portions of the optical radiation.

A well known version of time domain optical coherence reflectometry and tomography is the "common path" version, also known as autocorrelator or Fizeau interferometer based OCR/OCT. In this version, the reference and sample portions of the optical radiation do not travel along separate optical paths. Instead, a reference reflection is created in the sample optical path by introducing an optical inhomogenuity in the distal part of the delivering device, the inhomogenuity serving as a reference reflector. Resulting from that, the reference and sample portions of the optical radiation experience an axial shift only. The distance between the reference reflector and the front boundary of the longitudinal range of interest will be considered here as "reference offset". The entire combination of the sample portion of the optical radiation and axially shifted reference portion is combined with the replica of the same combination, shifted axially, so the reference portion of one replica has a time of flight (or optical path length) matching that of the sample portion of another replica. These portions interfere in a very similar way to the traditional "separate path" time domain optical coherence reflectometry/tomography embodiments. The interference signal is formed by a secondary interferometer, the two arms of which have an optical length difference ("interferometer offset") substantially equal to the reference offset. By scanning an optical delay between the two replicas, a time profile of the interference signal is obtained, which represents the in-depth profile of the coherent part of the reflected sample portion of optical radiation. The later is substantially equivalent to the profile obtained in traditional separate path embodiments.

Common path time domain reflectometry/tomography has a lot of intrinsic advantages over separate path time domain reflectometry/tomography. These advantages are based on the fact that reference and sample portions of the optical radiation propagate in the same optical path and therefore experience substantially identical delay, polarization distortions, optical dispersion, and the like. Therefore, the interference fringes are insensitive to the majority of the probe properties, including the optical fiber probe length, dispersion properties and polarization mismatch. In separate path time domain reflectometry/tomography, the length and dispersion of the sampling arm should be closely matched with the reference arm and the polarization mismatch should be prevented (using PM fiber or other means) or compensated (using polarization diversity receiver or other means).

A limitation to previously known common path time domain reflectometry/tomography devices is that the secondary interferometer necessarily includes Faraday mirrors to compensate for static and dynamic polarization changes in the interferometer arms. However, Faraday mirrors are known to be expensive, thus increasing the overall expenses for device manufacturing. In addition, the performance of Faraday mirrors is wavelength and temperature dependant, leading to a requirement of changing the Faraday mirrors when switching to a different wavelength and/or including additional tuning and temperature stabilizing means.

Another limitation to previously known common path time domain reflectometry/tomography devices is that the registered interference signal is responsive only to the non-depolarized portion, or in other words, responsive only to the parallel-polarized component of the optical radiation reflected or backscattered from the sample. The portion of the optical radiation depolarized by the sample and reflected or backscattered from it (the cross-polarized component), does not produce interference fringes and is not registered. However, in many cases OCR/OCT images created from the depolarized portion of the optical radiation demonstrate enhanced contrast and could be successfully used for biomedical diagnostics.

As will be appreciated by those skilled in the art, the concept of "parallel-polarized" and "cross-polarized" is applied here for elliptical polarization. "Parallel-polarized" is used for components with elliptical polarizations having the same eccentricity, same orientation of the long axis (ellipse tilt angle), and same rotation direction for the electric field. "Cross-polarized" is used for components with elliptical polarizations having the same eccentricity, orthogonal orientation of the long axis, and opposite rotation direction for the electric field. As in the case of linear or circular polarization these parallel-polarized components produce strongest interference, while cross-polarized components do not interfere at all.

Thus, there exists a need for a common path time domain OCR/OCT device that overcomes the above mentioned limitations by eliminating the necessity of using Faraday mirrors.

There also exists a need for a common path time domain OCR/OCT device that overcomes the above mentioned limitations by providing registration of the portion of the optical radiation depolarized by the sample, i.e. of the cross-polarized component of the optical radiation reflected or backscattered from the sample.

SUMMARY OF THE INVENTION

In accordance with the present invention, there are provided improved common path time domain OCR/OCT devices that use the advantages of a common path optical interferometer design overcoming the limitations of this approach.

In accordance with the present invention, there are provided common path time domain OCR/OCT devices that eliminate the necessity of using Faraday mirrors.

Further, in accordance with the present invention, there are provided common path time domain OCR/OCT devices that provide registration of a portion of the optical radiation depolarized by an associated sample, i.e. of a cross-polarized component of the optical radiation reflected or backscattered from an associated sample.

According to one aspect of the present invention, there is provided a common path time domain optical coherence reflectometer specified by a longitudinal range of interest at least partially overlapping with an associated sample. The longitudinal range of interest has at least a front boundary. The common path optical coherence time domain optical coherence reflectometer includes a source of optical radiation optically coupled with optical means that is adapted for producing two replicas of the optical radiation propagating therethrough. The two replicas are produced such that they have an optical path length difference. The optical means includes means for changing the optical path length difference for the two replicas of the optical radiation.

The common path time domain optical coherence reflectometer also includes a delivering device and a directional element. The directional element is optically coupled with the optical means and with the delivering device. The directional element is adapted for directing the two replicas of the optical radiation from the optical means to the proximal part of the delivering device. The delivering device is adapted for forming and delivering an optical radiation beam to an associated sample.

The delivering device includes a proximal part and a distal part. The distal part of the delivering device includes a reference reflector placed at a predetermined optical path length from the front boundary of a longitudinal range of interest of an associated sample. The optical path length difference for the two replicas of optical radiation is generally equal to the predetermined optical path length between the reference reflector and the front boundary of the longitudinal range of interest. The reference reflector serves as a combining element for producing a combination optical radiation by combining an optical radiation returning from an associated sample with a reference optical radiation reflected from the reference reflector.

The delivering device is further adapted for delivering the combination optical radiation to the directional element. The common path time domain optical coherence reflectometer further includes a time domain optoelectronic registering unit optically coupled with the directional element and including a data processing and displaying unit. The directional element is further adapted for directing the combination optical radiation to the time domain optoelectronic registering unit.

In one preferred embodiment of the common path time domain optical coherence reflectometer, the optical means includes a splitting element optically coupled with at least two optical paths. The splitting element is adapted for splitting the optical radiation into two replicas of the optical radiation. The at least two optical paths are adapted for the respective replicas of the optical radiation to propagate therethrough in a forward direction. The two optical paths have an optical path length difference generally equal to the predetermined optical path length between the reference reflector and the front boundary of the longitudinal range of interest. Preferably, at least one optical path of the optical means includes the means for changing the optical path length difference for the two replicas of the optical radiation propagating therethrough.

In accordance with one aspect of the present invention, the optical means in the common path time domain optical coherence reflectometer further includes a combining element optically coupled with the at least two optical paths. The combining element is adapted to direct the two replicas of the optical radiation to the directional element along a common optical path. At least one optical path of the optical means further includes a polarization controller adapted for controlling the polarization state of an associated replica of the optical radiation. In this case, the two replicas of the optical radiation are one of the following: parallel-polarized replicas of the optical radiation, and cross-polarized replicas of the optical radiation.

In accordance with another aspect of the present invention, the at least two optical paths of the optical means in the common path time domain optical coherence reflectometer are adapted for the respective replicas of the optical radiation to propagate therethrough in a backward direction toward the splitting element. The at least two optical paths of the optical means each include a mirror at its end. The splitting element further serves as a combining element adapted to direct the two replicas of the optical radiation to the directional element along a common optical path.

In another preferred embodiment of the common path time domain optical coherence reflectometer, the delivering device is an optical fiber probe. The optical fiber probe includes an optical fiber, the optical fiber including a tip. The tip of the optical fiber serves as the reference reflector.

According to another aspect of the present invention, the common path time domain optical coherence reflectometer further includes means for changing relative positions of the optical radiation beam being delivered to an associated sample, and the associated sample. In this embodiment, the common path time domain optical coherence reflectometer is part of a common path time domain device for optical coherence tomography.

In accordance with another aspect of the present invention, there is provided a common path time domain optical coherence tomography device specified by a longitudinal range of interest at least partially overlapping with an associated sample. The longitudinal range of interest has at least a front boundary. The common path optical coherence time domain optical coherence reflectometer includes a source of optical radiation optically coupled with optical means that is adapted for producing two replicas of the optical radiation propagating therethrough. The two replicas are produced such that they have an optical path length difference. The optical means includes means for changing the optical path length difference for the two replicas of the optical radiation.

The common path time domain optical coherence tomography device also includes a delivering device and a directional element. The directional element is optically coupled with the optical means and with the delivering device. The directional element is adapted for directing the two replicas of the optical radiation form the optical means to the proximal part of the delivering device. The delivering device is adapted for forming and delivering an optical radiation beam to an associated sample. The delivering device includes a proximal part and a distal part. The distal part of the delivering device includes a reference reflector placed at a predetermined optical path length from the front boundary of the longitudinal range of interest.

The optical path length difference for the two replicas of the optical radiation is generally equal to the predetermined optical path length between the reference reflector and the front boundary of the longitudinal range of interest. The reference reflector serves as a combining element for producing a combination optical radiation by combining an optical radiation returning from the associated sample with a reference optical radiation reflected from the reference reflector. The delivering device is further adapted for delivering the combination optical radiation to the directional element.

The common path time domain optical coherence tomography device further includes a time domain optoelectronic registering unit including a data processing and displaying unit and optically coupled with the directional element. The directional element is further adapted for directing the combination optical radiation to the time domain optoelectronic registering unit. The common path time domain optical coherence tomography device also includes means for changing relative positions of the optical radiation beam being delivered to the associated sample, and the associated sample.

Thus, in accordance with the subject invention, unlike previously known common path time domain OCT/OCR devices, optical radiation from a source is first split into two replicas, which are then delivered to an associated sample by a delivering device, the delivering device being, preferably, an optical fiber probe. The tip of the optical fiber probe serves as a reference reflector and also serves as a combining element that produces a combination optical radiation by combining an optical radiation returning from the associated sample with a reference optical radiation reflected from the reference reflector. The topology of the devices of the subject invention eliminates the necessity of using Faraday mirrors, and also allows for registering a cross-polarized component of the optical radiation reflected or backscattered from the associated sample, as well as a parallel-polarized component.

Still other objects and aspects of the present invention will become readily apparent to those skilled in this art from the following description wherein there are shown and described preferred embodiments of this invention, simply by way of illustration of the best modes suited for to carry out the invention. As it will be realized by those skilled in the art, the invention is capable of other different embodiments and its several details are capable of modifications in various obvious aspects all without from the invention. Accordingly, the drawings and description will be regarded as illustrative in nature and not as restrictive.

BRIEF DESCRIPTION OF DRAWINGS

The accompanying drawings incorporated in and forming a part of the specification, illustrate several aspects of the present invention, and together with the description serve to explain the principles of the invention. In the drawings.

DETAILED DESCRIPTION OF THE INVENTION

The subject application is directed to systems and methods for visualizing subsurface regions of samples, and more specifically, to a time domain optical coherence reflectometer and time domain optical coherence tomography device that provide internal depth profiles and depth images of samples. Modifications of the common path time domain optical coherence reflectometer are illustrated by means of examples of optical fiber devices being part of an apparatus for optical coherence tomography, although it is evident that they may be implemented with the use of bulk optic elements, and may be used as independent devices. The optical fiber implementation is preferable for use in medical applications, especially in endoscopy, where flexibility of the optical fiber provides convenient access to different tissues and organs, including internal organs via an endoscope. However, the whole device, or any part of it, can be implemented using traditional bulk optics: mirrors, prisms etc.

Figure 1:
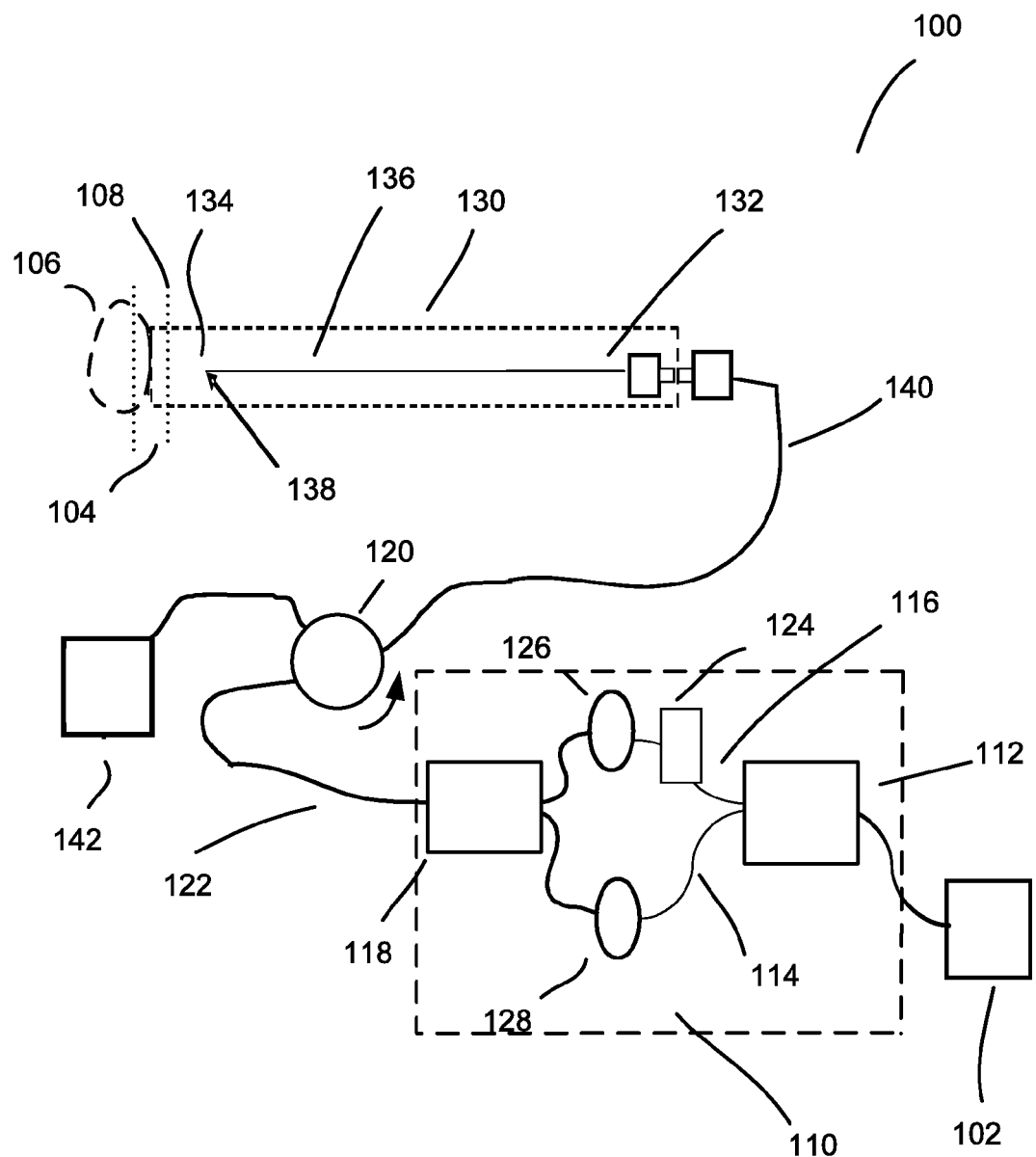
FIG. 1 is a block diagram of one preferred embodiment of the common path time domain optical coherence reflectometer of the invention.

Turning now to FIG. 1, there is shown a block diagram of an embodiment of the common path time domain optical coherence reflectometer 100. As shown in FIG. 1, the reflectometer 100 includes a source 102 of optical radiation optically coupled with optical means. In a preferred embodiment, the source 102 operates in the visible or near IR range. A skilled artisan will appreciate that the source 102 is, for example, and without limitation, a semiconductor superluminescent diode, doped-fiber amplified spontaneous emission superlum, solid state and fiberoptic femtosecond laser. The reflectometer 100 is specified by a longitudinal range of interest 104 at least partially overlapping with an associated sample 106. The longitudinal range of interest 104 has a front boundary 108. The optical means has at least two optical paths with an optical path length difference, and is suitably adapted for producing two replicas of the optical radiation propagating therethrough. For illustration purposes the optical means is depicted in FIG. 1 as an optical fiber Mach-Zehnder interferometer 110. A skilled artisan will appreciate that the optical means is capable of being implemented as any other optical interferometer known in the art.

The Mach-Zehnder interferometer 110 includes a splitting element 112 optically coupled with a first arm 114 and a second arm 116. The first and second arms 114, 116 have an optical path length difference (interferometer offset). The Mach-Zehnder interferometer 110 includes also a combining element 118. Those skilled in the art will recognize, that the splitting element 112 and the combining element 118 are capable of being implemented, for example, and without limitation, as 3 dB directional couplers. Those skilled in the art will also appreciate, that the embodiment as depicted in FIG. 1, is not limited to the use of 3 dB directional couplers. Other splitting and combining elements employing a different splitting rate may be suitably used without departing from the scope of the invention.

The combining element 118 of the Mach-Zehnder interferometer 110 is coupled to a directional element 120 through an optical fiber 122. A skilled artisan will appreciate, that the directional element 120 is capable of being implemented as a suitable circulator known in the art. At least one arm of the Mach-Zehnder interferometer includes a polarization controller 124.

In the embodiment of FIG. 1, the polarization controller 124 is included in the arm 116 of the Mach-Zehnder interferometer 110. At least one arm of the Mach-Zehnder interferometer 110 suitably includes means for changing the optical path length difference for the two replicas of optical radiation propagating therethrough. As will be recognized by those skilled in the art, the means for changing the optical path length difference for the two replicas of optical radiation is capable of being implemented as any suitable means known in the art, such as for example, and without limitation, a suitable delay line or a phase modulator. Thus, in the embodiment of FIG. 1, the arms 114, 116 include piezoelectric optical fiber delay elements 126, 128, respectively.

The common path time domain optical coherence reflectometer 100 also includes a delivering device coupled with the directional element 120. The embodiment of FIG. 1 illustrates the delivering device implemented as an optical fiber probe 130 that includes a proximal part 132 and a distal part 134. The optical fiber probe 130 includes an optical fiber 136. The tip 138 of the optical fiber 136 serves as a reference reflector and is placed at a predetermined optical path length from the front boundary 108 of the longitudinal range of interest 104. In the embodiment of FIG. 1, the optical fiber probe 130 is optically coupled with the directional element 120 through an optical fiber 140. Those skilled in the art will recognize, that above described Mach-Zehnder interferometer 110 is designed such that the arms 114, 116 have an optical path length difference for the two replicas of the optical radiation (interferometer offset) that is generally equal to the predetermined optical path length between the reference reflector (the tip 138 of the optical fiber 136) and the front boundary 108 of the longitudinal range of interest 104 (reference offset). As will be recognized by a skilled artisan, the optical fiber probe 130 also includes a lens system (not shown) in its distal part 134.

The common path time domain optical coherence reflectometer 100 further includes a time domain optoelectronic registering unit 142 optically coupled with the directional element 120. The time domain optoelectronic registering unit 142 includes a data processing and displaying unit (not shown in the drawing). A skilled artisan will appreciate that the time domain optoelectronic registering unit 142 is capable of being implemented as any suitable registering unit known in the art.

A slow delay line suitably adapted to control the axial position of the observation zone is capable of being introduced in any of the arms of the Mach-Zehnder interferometer 110 (not shown in the drawing).

Figure 2:
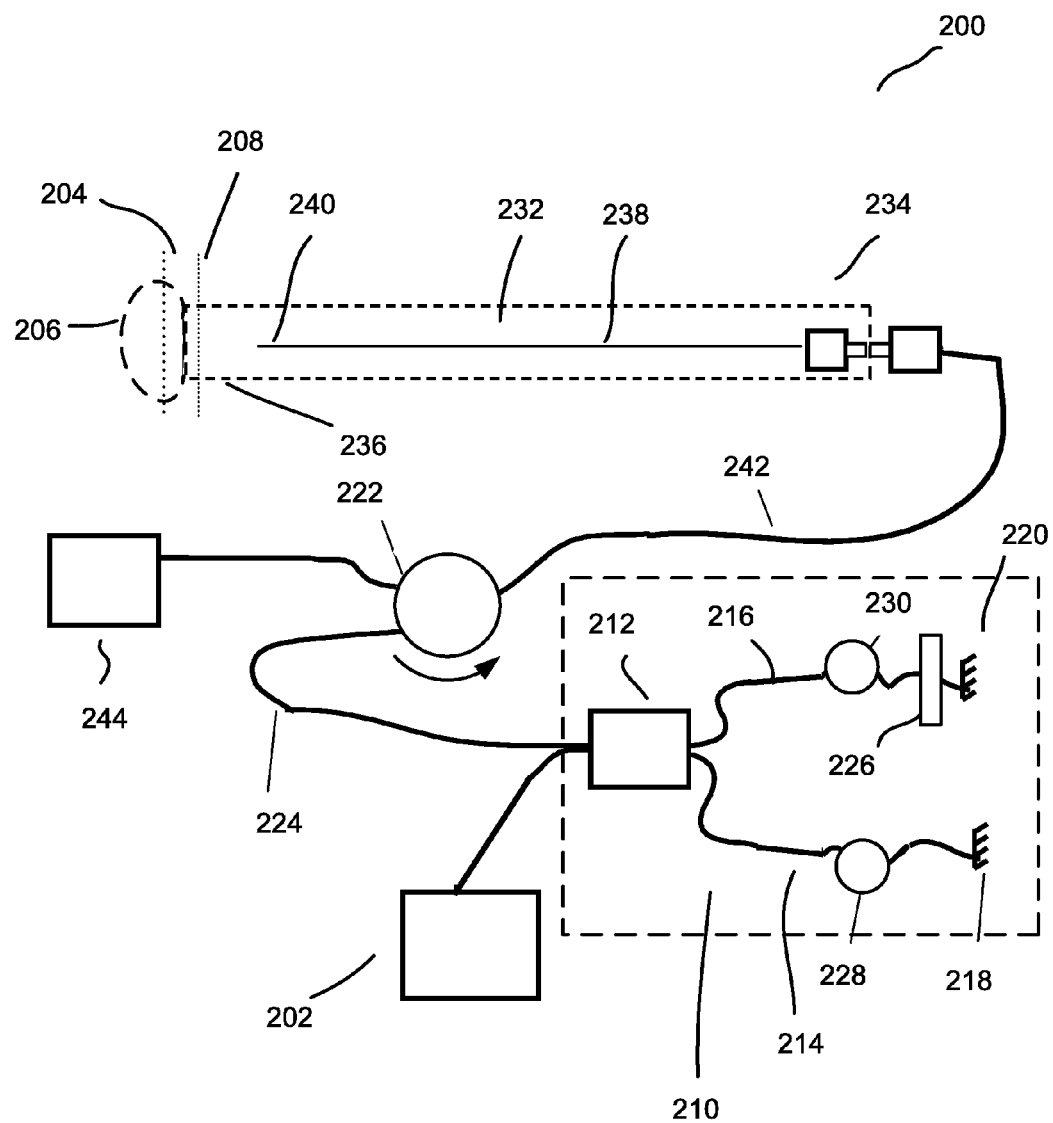
FIG. 2 is a block diagram of another preferred embodiment of the common path time domain optical coherence reflectometer of the invention.

Turning now to FIG. 2, there is shown a block diagram of another embodiment of the common path time domain optical coherence reflectometer 200. As shown in FIG. 2, the reflectometer 200 includes a source 202 of optical radiation optically coupled with optical means. In a preferred embodiment, the source 202 operates in the visible or near IR range. A skilled artisan will appreciate that the source 202 is capable of being implemented analogous to the source 102 of the embodiment, as depicted in FIG. 1. The reflectometer 200 is specified by a longitudinal range of interest 204 at least partially overlapping with an associated sample 206. The longitudinal range of interest 204 has a front boundary 208. The optical means has at least two optical paths with an optical path length difference, and is suitably adapted for producing two replicas of the optical radiation propagating therethrough. For illustration purposes the optical means is depicted in FIG. 2 as an optical fiber Michelson interferometer 210. The Michelson interferometer 210 includes a splitting and combining element 212 optically coupled with a first arm 214 and a second arm 216. The Michelson interferometer 210 includes also mirrors 218, 220 placed at the distal end of the first and second arms 214, 216, respectively. Those skilled in the art will recognize, that splitting and combining element 212 is implemented, for example, and without limitation, as a 3 dB directional coupler. Those skilled in the art will also appreciate, that the embodiment as depicted in FIG. 2, is not limited to the use of a 3 dB directional coupler. Other splitting elements employing a different splitting rate may be suitably used without departing from the scope of the invention.

In the embodiment of FIG. 2, the splitting and combining element 212 of the Michelson interferometer 210 is coupled to a directional element 222 through an optical fiber 224. In a preferred embodiment at least one arm of the Michelson interferometer 210 includes a polarization controller 226. In the embodiment of FIG. 2, the polarization controller 226 is included in the arm 216 of the Michelson interferometer 210. A skilled artisan will appreciate that in this case at least one mirror of the mirrors 218, 220 is implemented as a regular mirror. Preferably, at least one arm of the Michelson interferometer 210 includes means for changing the optical path length difference for the two replicas of optical radiation propagating therethrough. As will be recognized by those skilled in the art, the means for changing the optical path length difference for the two replicas of optical radiation is capable of being implemented analogous to that in the embodiment of FIG. 1. Thus, in the embodiment of FIG. 2, the arms 214, 216 include piezoelectric optical fiber delay elements 228, 230, respectively.

The common path time domain optical coherence reflectometer 200 also includes a delivering device coupled with the directional element 222. The embodiment of FIG. 2 illustrates the delivering device implemented as an optical fiber probe 232 that includes a proximal part 234 and a distal part 236. The optical fiber probe 232 includes an optical fiber 238. The tip 240 of the optical fiber 238 serves as a reference reflector. The tip 240 of the optical fiber 238 is placed at a predetermined optical path length from the front boundary 208 of the longitudinal range of interest 204. In the embodiment of FIG. 2 the optical fiber probe 232 is optically coupled with the directional element 222 through an optical fiber 242. Those skilled in the art will recognize, that above described Michelson interferometer 210 is designed such that the arms 214, 216 have an optical path length difference for the two replicas of the optical radiation (interferometer offset) that is generally equal to the predetermined optical path length between the reference reflector (the tip 240 of the optical fiber 238) and the front boundary 208 of the longitudinal range of interest 204 (reference offset). A skilled artisan will recognize, that the optical fiber probe 232 the same as the optical fiber probe 130 in the embodiment of FIG. 1, also includes a lens system (not shown) in its distal part 236.

The common path time domain optical coherence reflectometer 200 further includes a time domain optoelectronic registering unit 244 optically coupled with the directional element 222. The time domain optoelectronic registering unit 244 includes a data processing and displaying unit (not shown in the drawing). A skilled artisan will appreciate that the time domain optoelectronic registering unit 244 is capable of being implemented analogous to the registering unit 140 of the embodiment of FIG. 1.

A slow delay line suitably adapted to control the axial position of the observation zone is capable of being introduced in any of the arms of the Michelson interferometer 210 (not shown in the drawing). As will be appreciated by a skilled artisan, in the embodiment of FIG. 2, a suitable isolator or circulator may be required between the source 202 of optical radiation and the Michelson interferometer 210.

In accordance with another aspect of the invention, both the embodiment of FIG. 1, and the embodiment of FIG. 2, are capable of further including means for changing relative positions of the optical radiation beam being delivered to an associated sample, and the associated sample (not shown in the drawing), the common path time domain optical coherence reflectometer being part of a common path time domain device for optical coherence tomography. Those skilled in the art will recognize that the means for changing relative positions of the optical radiation beam being delivered to the associated sample, and the associated sample is suitably capable of being implemented in any way known in the art, for example and without limitation, as a lateral scanner incorporated into the delivering device, or as an element for changing the position of the associated sample.

Referring now to operation of the common path time domain optical coherence reflectometer 100 in accordance with the present invention shown in FIG. 1, the operation of the reflectometer 100 commences by placing the delivering device, preferably implemented as the optical fiber probe 130, such that there exists a predetermined optical path length between the tip 138 of the optical fiber 136, the tip 138 serving as a reference reflector, and the front boundary 108 of the longitudinal range of interest 104 (reference offset). Next, an optical radiation from the source 102 is directed to the Mach-Zehnder interferometer 110. The splitting element 112 of the Mach-Zehnder interferometer 110 splits the optical radiation into two replicas. One replica propagates along the arm 114, while the other replica propagates along the arm 116. As stated above, the optical path length difference of the arms 114, 116 is generally equal to the predetermined optical path length between the reference reflector (tip 138 of the optical fiber 136) and the front boundary 108 of the longitudinal range of interest 104 (reference offset).

The two replicas are combined by the combining element 118 to enter the optical fiber probe 130 through the common optical fiber 122, the directional element 120, and the common optical fiber 140. The optical fiber probe 130 is adapted for forming and delivering an optical radiation beam to the associated sample 106. Thus, one part of a portion of the optical radiation beam corresponding to each replica is delivered to the associated sample 106 and is reflected or backscattered from it (the sample portion). Another part of each portion of the optical radiation that enters the optical fiber probe 130 does not reach the associated sample 106, but is instead reflected at the tip 138 of optical fiber 136 of the optical fiber probe 130, at some distance from the associated sample 106 (the reference portion). Those skilled in the art will appreciate that due to the mentioned above relationship between the reference offset and the interferometer offset, the tip 138 of optical fiber 136 produces a combination optical radiation in a manner similar to that of the directional coupler in the previously known common path time domain optical coherence reflectometer with a secondary interferometer. The tip 138 of the optical fiber 136 combines an optical radiation returning from the associated sample 106 of one replica of optical radiation with a reference optical radiation being reflected from the tip 138 of the other replica.

Those skilled in the art will appreciate, that the polarization controller 124 included in the arm 116 of the Mach-Zehnder interferometer 110 is capable of being aligned just the once, since any bending of the optical fiber probe 130 has no influence on the replicas of the optical radiation propagating through the Mach-Zehnder interferometer 110. The manner in which the polarization controller 124 is aligned depends on the type of images chosen for being registered. In accordance with one aspect of the invention, the polarization controller 124 is aligned such that the two replicas of the optical radiation are parallel-polarized as they leave the Mach-Zehnder interferometer 110 and enter the directional element 120. In this case, the time domain optoelectronic registering unit 142 registers a combination optical radiation responsive to a portion of the reflected optical radiation that is not depolarized by the associated sample 106. The depolarized portion of the optical radiation reflected from the associated sample 106 does not produce interference fringes and is not registered. In accordance with another aspect of the invention, the polarization controller 124 is aligned such that the two replicas of the optical radiation are cross-polarized as they leave the Mach-Zehnder interferometer 110, so the system becomes a so-called "cross-polarization" OCR/OCT device. In the latter case, the time domain optoelectronic registering unit 142 registers a combination optical radiation responsive only to a portion of the reflected optical radiation that is depolarized by the associated sample 106. The non-depolarized portion of the optical radiation reflected from the associated sample 106 does not produce interference fringes and is not registered.

Referring now to operation of the common path time domain optical coherence reflectometer 200 in accordance with the present invention shown in FIG. 2, those skilled in the art will recognize, that the operation of the reflectometer 200 proceeds in the same manner as the operation of the reflectometer 100 depicted in FIG. 1, as described in detail above. A skilled artisan will also appreciate, that in the embodiment with the mirrors 218, 220 implemented as Faraday mirrors, the time domain optoelectronic registering unit 244 registers a combination optical radiation responsive to a portion of the reflected optical radiation that is not depolarized by the associated sample 206. The depolarized portion of the optical radiation reflected from the associated sample 206 does not produce interference fringes and is not registered. In the embodiment with the polarization controller 226 included in the arm 216, the operation of the reflectometer 200 is analogous to the reflectometer 100 of FIG. 1.

Figure 3A:
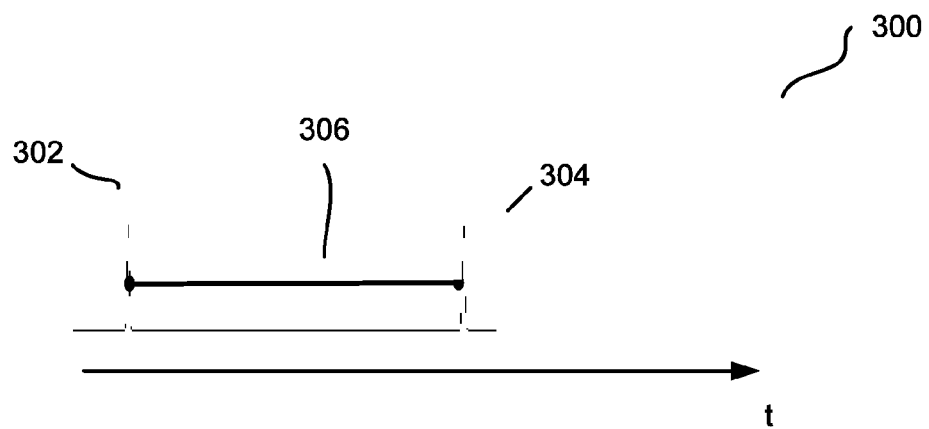
FIG. 3a illustrates two replicas of the optical radiation entering the optical fiber probe in the embodiment of the subject invention shown in FIG. 1.
Figure 3B:
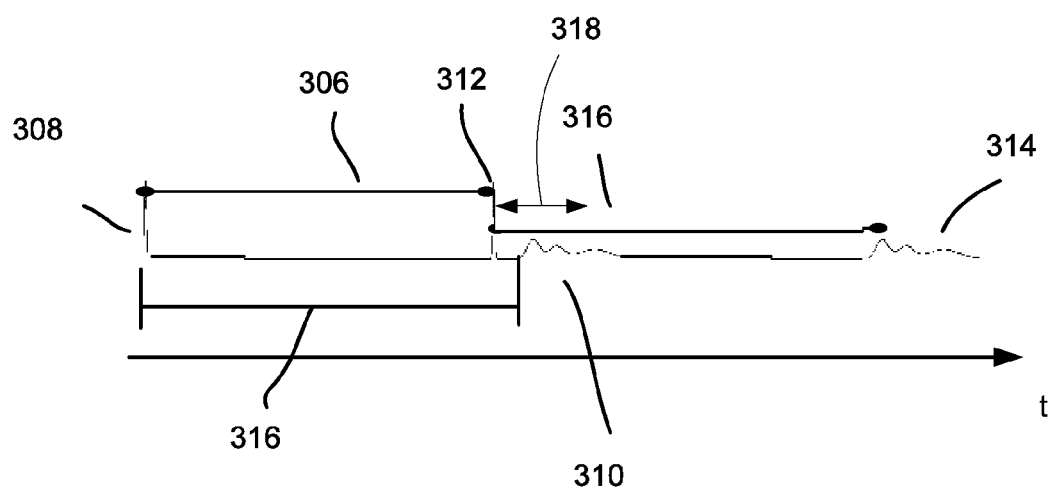
FIG. 3b is an illustration of the two replicas of the optical radiation after each of them was split into two portions (a reference portion and a sample portion) by the tip of the optical fiber in the embodiment of the subject invention shown in FIG. 1.

Turning now to FIG. 3, there is shown an illustration 300 of producing a combination optical radiation in accordance with the present invention with reference to the embodiment depicted in FIG. 1. For illustration purposes the optical radiation is represented by an imaginary short pulse propagating therethrough and placed along a time axis t in FIG. 3. Thus, FIG. 3a illustrates the optical radiation entering the optical fiber probe 130 through the directional element 120 of FIG. 1, after the optical radiation from the source 102 is divided into two replicas shifted along the time axis by the Mach-Zehnder interferometer 110. The two replicas are illustrated in FIG. 3a as respective short pulses 302 and 304. As will be recognized by a skilled artisan, the time shift between the two replicas of the optical radiation is defined by the interferometer offset 306. FIG. 3b illustrates the two replicas after each of them was split into two portions (a reference portion and a sample portion) by the tip 138 of the optical fiber 136 of the optical fiber probe 130. As shown in FIG. 3b, the reference portion 308 of the first replica has a shift (reference offset 316) with respect to the sample portion 310 of the same replica. Also, the reference portion 312 of the second replica has a shift (reference offset 316) with respect to the sample portion 314 of the same replica. Those skilled in the art will appreciate that reference portion of one replica interferes with the sample portion of the other replica in the same manner as in a previously known common path time domain optical coherence reflectometer with a secondary interferometer. Arrows 318 illustrated changing of the interferometer offset for obtaining an in-depth profile of an associated sample 106 in the manner known in the art.

As will be recognized by those skilled in the art, the illustration of producing a combination optical radiation in accordance with the present invention with reference to the embodiment depicted in FIG. 1 provided herein, is equally applicable to the embodiment shown in FIG. 2.

The foregoing description of the preferred embodiments of the subject application has been presented for purposes of illustration and description. It is not intended to be exhaustive or to limit the subject application to the precise form disclosed. Obvious modifications or variations are possible in light of the above teachings. The embodiments were chosen and described to provide the best illustration of the principles of the subject application and its practical application to thereby enable one of ordinary skill in the art to use the subject application in various embodiments and with various modifications as are suited to the particular use contemplated. All such modifications and variations are within the scope of the subject application as determined by the appended claims when interpreted in accordance with the breadth to which they are fairly, legally and equitably entitled.

What is claimed is:

1. A common path time domain optical coherence reflectometer specified by a longitudinal range of interest having at least a front boundary, and at least partially overlapping with an associated sample, comprising:
    a source of optical radiation;
    an optical device optically coupled with the source of optical radiation, the optical device being configured to produce two replicas of the optical radiation propagating therethrough having an optical path length difference, the optical device including means for changing the optical path length difference for the two replicas of the optical radiation;
    a delivering device configured to form and deliver an optical radiation beam to an associated sample, the delivering device including a proximal part and a distal part, the distal part of the delivering device including a reference reflector placed at a predetermined optical path length from the front boundary of a longitudinal range of interest of an associated sample;
    a directional element configured to direct the two replicas of the optical radiation to the proximal part of the delivering device, and optically coupled with the optical device and with the delivering device; and
    a time domain optoelectronic registering unit including a data processing and displaying unit, and optically coupled with the directional element;
    wherein the optical path length difference for the two replicas of the optical radiation is generally equal to the predetermined optical path length between the reference reflector and the front boundary of the longitudinal range of interest;
    wherein the reference reflector serves as a combining element for producing a combination optical radiation by combining an optical radiation returning from an associated sample with a reference optical radiation reflected from the reference reflector;
    wherein the delivering device is further adapted for delivering the combination optical radiation to the directional element, and
    wherein the directional element is further adapted for directing the combination optical radiation to the time domain optoelectronic registering unit.

2. The common path time domain optical coherence reflectometer of claim 1 wherein the optical device further comprises a splitting element optically coupled with at least two optical paths, wherein the splitting element is configured to split the optical radiation into two replicas of the optical radiation, wherein the at least two optical paths are adapted for the respective replicas of the optical radiation to propagate therethrough in a forward direction, and wherein the means for changing the optical path length difference for the two replicas of the optical radiation is part to at least one of the at least two optical paths.

3. The common path time domain optical coherence reflectometer of claim 2 wherein the optical device further includes a combining element optically coupled with the at least two optical paths, and wherein the combining element is configured to direct the two replicas of the optical radiation to the directional element along a common optical path.

4. The common path time domain optical coherence reflectometer of claim 3 wherein at least one optical path of the optical device further includes a polarization controller configured to control the polarization state of an associated replica of the optical radiation, and wherein the two replicas of the optical radiation are one of the following: parallel-polarized replicas of the optical radiation, and cross-polarized replicas of the optical radiation.

5. The common path time domain optical coherence reflectometer of claim 2 wherein the at least two optical paths of the optical device are further positioned for the respective replicas of the optical radiation to propagate therethrough in a backward direction toward the splitting element, wherein the at least two optical paths of the optical means each include a mirror at its distal end, and wherein the splitting element further serves as a combining element adapted to direct the two replicas of the optical radiation to the directional element along a common optical path.

6. The common path time domain optical coherence reflectometer of claim 5 wherein the mirror included in at least one optical path of the at least two optical paths is a regular mirror, wherein at least one optical path of the optical device further includes a polarization controller adapted for controlling the polarization state of an associated replica of the optical radiation, and wherein the two replicas of the optical radiation are one of the following: parallel-polarized replicas of the optical radiation, and cross-polarized replicas of the optical radiation.

7. The common path time domain optical coherence reflectometer of claim 5 wherein the mirror included in each of the at least two optical paths is a Faraday mirror, and wherein the two replicas of the optical radiation are parallel-polarized replicas of the optical radiation.

8. The common path time domain optical coherence reflectometer of claim 1 wherein the delivering device is an optical fiber probe.

9. A common path time domain optical coherence tomography device, specified by a longitudinal range of interest having at least a front boundary, and at least partially overlapping with an associated sample, comprising:
    a source of optical radiation;
    an optical device optically coupled with the source of optical radiation and configured to produce two replicas of the optical radiation propagating therethrough having an optical path length difference, the optical device including means for changing the optical path length difference for the two replicas of the optical radiation;
    a delivering device configured to form and deliver an optical radiation beam to an associated sample, the delivering device including a proximal part and a distal part, the distal part of the delivering device including a reference reflector placed at a predetermined optical path length from the front boundary of a longitudinal range of interest of an associated sample;

a directional element optically coupled with the optical means and with the delivering device, and configured to direct the two replicas of optical radiation from the optical means to the proximal part of the delivering device;

a time domain optoelectronic registering unit optically coupled with the directional element and including a data processing and displaying unit;

wherein the optical path length difference for the two replicas of optical radiation is generally equal to the predetermined optical path length between the reference reflector and the front boundary of the longitudinal range of interest;

wherein the reference reflector serves as a combining element for producing a combination optical radiation by combining an optical radiation returning from an associated sample with a reference optical radiation reflected from the reference reflector;

wherein the delivering device is further adapted for delivering the combination optical radiation to the directional element, and wherein the directional element is further adapted for directing the combination optical radiation to the time domain optoelectronic registering unit.

10. The common path time domain optical coherence reflectometer of claim 9 wherein the optical fiber probe comprises an optical fiber including a tip, and wherein the tip of the optical fiber serves as the reference reflector.

11. The common path time domain optical coherence tomography device of claim 9 wherein the optical device further comprises a splitting element optically coupled with at least two optical paths, wherein the splitting element is configured to split the optical radiation into two replicas of the optical radiation, wherein the at least two optical paths are positioned for the respective replicas of the optical radiation to propagate therethrough in a forward direction, and wherein the means for changing the optical path length difference for the two replicas of the optical radiation is part to at least one of the at least two optical paths.

12. The common path time domain optical coherence tomography device of claim 11 wherein the optical device further includes a combining element optically coupled with the at least two optical paths, and wherein the combining element is configured to direct the two replicas of the optical radiation to the directional element along a common optical path.

13. The common path time domain optical coherence tomography device of claim 12 wherein at least one optical path of the optical device further includes a polarization controller configured to control the polarization state of an associated replica of the optical radiation, and wherein the two replicas of the optical radiation are one of the following: parallel-polarized replicas of the optical radiation, and cross-polarized replicas of the optical radiation.

14. The common path time domain optical coherence tomography device of claim 11 wherein the at least two optical paths of the optical means are further positioned for the respective replicas of the optical radiation to propagate therethrough in a backward direction toward the splitting element, wherein the at least two optical paths of the optical device each include a mirror at its distal end, and wherein the splitting element further serves as a combining element adapted to direct the two replicas of the optical radiation to the directional element along a common optical path.

15. The common path time domain optical coherence tomography device of claim 14 wherein the mirror included in at least one optical path of the at least two optical paths is a regular mirror, wherein at least one optical path of the optical means further includes a polarization controller configured to control the polarization state of an associated replica of the optical radiation, and wherein the two replicas of the optical radiation are one of the following: parallel-polarized replicas of the optical radiation, and cross-polarized replicas of the optical radiation.

16. The common path time domain optical coherence tomography device of claim 14 wherein the mirror included in each of the at least two optical paths is a Faraday mirror, and wherein the two replicas of the optical radiation are parallel-polarized replicas of the optical radiation.

* * * * *